(12) United States Patent
Fritz et al.

(10) Patent No.: US 11,560,344 B2
(45) Date of Patent: Jan. 24, 2023

(54) METHOD AND SYSTEM FOR PRODUCING ONE OR MORE OLEFINS

(71) Applicant: LINDE GmbH, Pullach (DE)

(72) Inventors: Helmut Fritz, Munich (DE); Andreas Meiswinkel, Rimsting (DE); Martin Schubert, Munich (DE); Mathieu Zellhuber, Martinsried (DE); Nicole Schödel, Munich (DE); Sonja Schulte, Wolfratshausen (DE); Anina Wöhl, Munich (DE)

(73) Assignee: LINDE GmbH, Pullach (DE)

( * ) Notice: Subject to any disclaimer, the term of this patent is extended or adjusted under 35 U.S.C. 154(b) by 0 days.

(21) Appl. No.: 17/439,032

(22) PCT Filed: Mar. 4, 2020

(86) PCT No.: PCT/EP2020/055737
§ 371 (c)(1),
(2) Date: Sep. 14, 2021

(87) PCT Pub. No.: WO2020/187572
PCT Pub. Date: Sep. 24, 2020

(65) Prior Publication Data
US 2022/0153661 A1 May 19, 2022

(30) Foreign Application Priority Data

Mar. 15, 2019 (EP) ..................................... 19163320
Mar. 15, 2019 (EP) ..................................... 19163321

(51) Int. Cl.
*C07C 5/48* (2006.01)
*B01J 23/72* (2006.01)
(Continued)

(52) U.S. Cl.
CPC ................. *C07C 5/48* (2013.01); *B01J 23/72* (2013.01); *B01J 23/74* (2013.01); *C07C 2/84* (2013.01);
(Continued)

(58) Field of Classification Search
CPC .. C07C 5/48; C07C 2/84; C07C 7/167; C07C 2523/72; C07C 2523/74; C07C 2521/04;
(Continued)

(56) References Cited

U.S. PATENT DOCUMENTS 2,381,707 A    8/1945    Wood et al.
2,953,608 A    9/1960    Fernald
(Continued)

FOREIGN PATENT DOCUMENTS

CA          3057248 A1    10/2018
DE    102005000798 A1    7/2006
(Continued)

OTHER PUBLICATIONS

PCT/EP2020/055737 International Search Report dated May 28, 2020, 2 pages.
(Continued)

*Primary Examiner* — Ali Z Fadhel
(74) *Attorney, Agent, or Firm* — Lathrop GPM LLP

(57) ABSTRACT

A process (100) is proposed for the production of one or more olefins, in which a reaction feed containing oxygen and one or more paraffins is formed and in which a part of the oxygen in the reaction feed is reacted with a part of the one or more paraffins to form the one or more olefins by an oxidative process, to obtain a process gas, the process gas containing at least the unreacted part of the one or more paraffins and oxygen, the one or more olefins, one or more acetylenes, carbon dioxide and water. The process comprises subjecting the process gas or a gas mixture formed using at
(Continued)

least a part of the process gas partially or completely to a condensate separation (2), a compression (3), an at least partial removal (4) of the oxygen and acetylene(s) and to one or more stages of a carbon dioxide removal (5) in the order given herein, wherein the at least partial removal (4) of the oxygen and of the acetylene(s) is performed at the same time and by a catalytic conversion using a catalyst comprising copper oxide or ruthenium, and wherein the catalytic conversion is performed at least in part in the form of a hydrogenation. A corresponding plant is also the subject of the present invention.

10 Claims, 2 Drawing Sheets

(51) Int. Cl.
 *B01J 23/74* (2006.01)
 *C07C 2/84* (2006.01)
 *C07C 7/167* (2006.01)
(52) U.S. Cl.
 CPC .......... *C07C 7/167* (2013.01); *C07C 2523/72* (2013.01); *C07C 2523/74* (2013.01)
(58) Field of Classification Search
 CPC ..... C07C 2523/889; C07C 7/005; C07C 7/09; C07C 7/148; C07C 7/14858; C07C 7/163; C07C 2/282; B01J 23/72; B01J 23/74; Y02P 20/52
 See application file for complete search history.

(56) References Cited

U.S. PATENT DOCUMENTS

| | | |
|---|---|---|
| 3,912,789 A | 10/1975 | Frevel et al. |
| 4,034,062 A | 7/1977 | Krueger |
| 4,035,433 A | 7/1977 | Drehman et al. |
| 4,049,743 A | 9/1977 | Drehman et al. |
| 5,446,232 A | 8/1995 | Chen et al. |
| 2005/0065392 A1* | 3/2005 | Peterson .................. C07C 2/80 585/324 |
| 2019/0389788 A1* | 12/2019 | Mamedov ................. C01B 3/36 |
| 2020/0002251 A1* | 1/2020 | Mitkidis ................... C07C 5/48 |
| 2020/0223768 A1* | 7/2020 | Van Rossum ............. C07C 5/48 |
| 2020/0223769 A1* | 7/2020 | Calvo ....................... C07C 5/48 |

FOREIGN PATENT DOCUMENTS

| | | |
|---|---|---|
| WO | WO 2010115108 A1 | 4/2010 |
| WO | WO 2015081122 A2 | 11/2014 |
| WO | WO 2015113747 A1 | 8/2015 |
| WO | WO 2018153831 A1 | 8/2018 |

OTHER PUBLICATIONS

PCT/EP2020/055737 International Preliminary Report on Patentability dated Sep. 16, 2021, 6 pages.
Gulf Cooperation Council Patent Application No. GC 2020-39383 Examination Report dated Aug. 5, 2021, 5 pages.

\* cited by examiner

METHOD AND SYSTEM FOR PRODUCING ONE OR MORE OLEFINS

The present invention relates to a process for the production of one or more olefins and to a corresponding plant according to the preambles of the independent claims.

PRIOR ART

Oxidative Dehydrogenation (ODH) of paraffins with two to four carbon atoms is basically known. In ODH, the paraffins mentioned above are reacted with oxygen to form, among others, olefins with the same carbon number and water.

ODH may be advantageous over more established olefin production processes such as steam cracking or catalytic dehydrogenation. Due to the exothermic nature of the reactions involved, there is no thermodynamic equilibrium limitation. ODH can be performed at comparatively low reaction temperatures. In principle, no regeneration of the catalysts used is necessary, since the presence of oxygen allows in-situ regeneration. Finally, in contrast to steam cracking, smaller quantities of worthless by-products such as coke are formed.

For further details concerning ODH, reference is made to relevant technical literature, for example Ivars, F. and López Nieto, J. M., Light Alkanes Oxidation: Targets Reached and Current Challenges, in: Duprez, D. and Cavani, F. (eds.), Handbook of Advanced Methods and Processes in Oxidation Catalysis: From Laboratory to Industry, London 2014: Imperial College Press, pages 767 to 834, or Gartner, C. A. et al., Oxidative Dehydrogenation of Ethane: Common Principles and Mechanistic Aspects, ChemCatChem, Vol. 5, No. 11, 2013, pages 3196 to 3217.

ODH is also used, for example, in the procedures disclosed in WO 2018/153831 A1, WO 2010/115108 A1, DE 10 2005 000 798 A1 and WO 2015/113747 A1. WO 2015/113747 A1 already discloses a water separation upstream of a catalytic removal of carbon monoxide and oxygen from a product mixture of ODH, which is again proposed in WO 2018/153831 A1.

The present invention relates in particular to the production of ethylene by ODH of ethane (ODH-E), but may also be used for other process variants of ODH and other processes, such as Oxidative Coupling of Methane (OCM), in which the problems explained below partly arise in the same or comparable manner. In oxidative coupling of methane, a methane-rich and an oxygen-rich stream are fed into a reactor, where the oxygen of the oxygen-rich stream and part of the methane of the methane-rich stream react to form higher hydrocarbons, in particular the target product ethylene, with the formation of water and by-products. The oxidative coupling of methane is disclosed in WO 2015/081122 A3.

A minimum concentration of oxygen is required for the sustained activity of the catalysts used in ODH, especially in ODH-E, which are in particular MoVNbTeOx catalysts of basically known type. In this way a reduction and thus a loss of performance of the catalysts can be avoided. For this reason, ODH generally does not operate with a complete oxygen conversion and the gas mixture withdrawn from a corresponding reactor contains oxygen. The latter may also be the case in other procedures, for example in OCM.

In addition, higher conversions in ODH result in significant amounts of carbon monoxide and carbon dioxide and small amounts of acetylene as by-products. Especially under industrially relevant reaction conditions, significant amounts of the respective carboxylic acids of the paraffins used can also be formed as by-products. Corresponding components are therefore advantageously separated from each other or from the desired main product(s) in a separation section or are removed by chemical reaction or converted into more easily removable components. The present invention concerns in particular the removal of oxygen and acetylene(s) from a corresponding gas mixture. A gas mixture obtained in OCM likewise may contain corresponding components and they are separated.

Processes known from other areas of technology for removing acetylene from gas mixtures are not transferable to ODH or ODH-E and, to that extent, comparable processes to OCM, for the reasons explained in detail below. The invention therefore has the object of indicating measures which allow acetylene and oxygen to be removed in a beneficial manner from a gas mixture obtained in particular by means of ODH or ODH-E or OCM. Catalytic removal is to be used for this purpose, but in a manner that is advantageous compared to the cited prior art.

DISCLOSURE OF THE INVENTION

Against this background, the present invention proposes a process for the production of one or more olefins and a corresponding plant with the features of the independent claims. Advantageous embodiments of the present invention are the subject of the dependent patent claims and of the following description.

Advantages of the Invention

Figure 1:
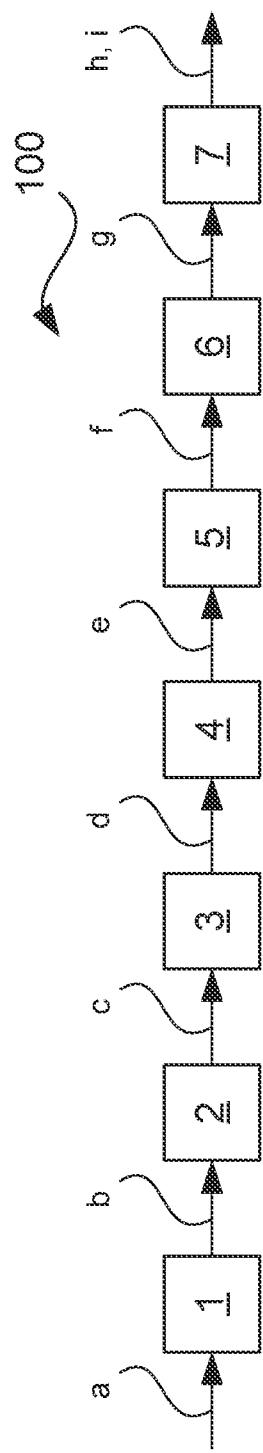
FIG. 1 illustrates a method according to an embodiment

According to the invention, an optimized sequence for the removal of unwanted components from a process gas of an oxidative process such as ODH, in particular ODH-E, but also for example OCM, is provided, which enables a functional, safe and efficient operation at minimal investment costs. The unwanted components are oxygen and acetylene(s). Which acetylenes are present depends in particular on the chain length of the paraffins used. In ODH-E and OCM this is acetylene (ethyne). For the sake of simplicity, the term "acetylene" will be used below, even if several acetylenes (alkynes) are present. Furthermore, the following always refers to a "removal" of oxygen and acetylene(s), even if these components are only removed to a certain extent, in particular to a predominant part, i.e. in particular more than 90%, 95% or 99%. (All percentages used here can refer to the molar fraction, the mass fraction or the volume fraction). Inventive aspects concern as well the use of specific catalysts and configurations of specific catalytic conditions which, in connection with an oxidative process such as ODH or ODH-E or OCM, are particularly suitable for the purposes explained, wherein according to the invention at least partially a hydrogenation is carried out.

In the following, the positioning or arrangement of an oxygen and acetylene removal step in a corresponding separation sequence, which is carried out according to the invention, is described first, followed by a description of the catalysts used according to the invention and the corresponding catalysis conditions. It should be expressly emphasized that the features designated as optional or advantageously provided need not be part of the invention and that the present invention can also only refer to the features designated as being in accordance with the invention.

By positioning the oxygen and acetylene removal step in accordance with the invention, the present invention particularly takes into account that the introduction of oxygen-containing gas into an amine scrubber, as typically used for the removal of carbon dioxide from a process gas of an ODH or ODH-E or an OCM, represents a considerable risk for the long-term operability of such process units, since undesired side reactions can occur there due to the introduction of oxygen. The same applies in general to chemical carbon dioxide scrubbing, for example also to typically used amine scrubbing.

The present invention also takes into account, by positioning the oxygen and acetylene removal step according to the invention, that a certain degree of concentration and partial pressure increase is advantageous for acetylene removal. Since acetylenes only are present at the reactor outlet in comparatively low concentrations of approx. 100 to 200 ppm volume fraction, a certain degree of concentration and partial pressure increase is advantageous. Conversely, the presence of significant amounts of water is not advantageous, since this can lead to further side reactions.

Basically, it should be noted that in the course of a separation sequence for the production of ethylene from a process gas from ODH-E (process variants for the conversion of higher paraffins by ODH and OCM are affected in the same way), without appropriate oxygen removal, a gradual enrichment of oxygen in the separation sequence takes place, which at a certain point leads to an ignitable mixture. The present invention also takes this into account by positioning the oxygen and acetylene removal step according to the invention. The oxygen removal is advantageously carried out at a point in the separation sequence where a critical oxygen content has not yet been reached.

Due to other by-products present in the process gas, it is to be expected that the chemical reaction of acetylene during its removal will produce further components to be separated from ethylene or other olefins. Therefore, the positioning of the oxygen and acetylene removal step according to the invention ensures that such components can be separated in the further separation sequence without significant additional effort.

Finally, for the highest possible energy efficiency, it is advantageous for the oxygen and acetylene removal to be carried out at a point in the process where the process gas conditions are close to those most favourable to the catalytic reactions for oxygen and acetylene removal. This can be ensured by positioning the oxygen and acetylene removal step according to the invention.

Applied to ODH-E or OCM, none of the hydrogenation concepts known for steam cracking processes fulfils the requirements explained above, but these are met by the positioning of the oxygen and acetylene removal step which is carried out according to the invention. However, the same applies in view of a process proposed in WO 2010/115108 A1, in which oxygen is removed directly downstream of the ODH reactor in a separate reactor in which a hydrogenation catalyst is provided, by means of which acetylenes, for example, can also be hydrogenated.

The positioning of the oxygen and acetylene removal step according to the invention in the manner explained allows the products formed in the reaction unit to be separated from the main product, in the case of ODH-E or OCM ethylene, together with the other process gas present components without additional constructive effort. For this purpose, processes or process steps known per se are used, e.g. an amine or caustic wash, which operate in an aqueous medium and are therefore not affected by the water formed in the oxygen and acetylene removal step.

In contrast to WO 2010/115108 A1, the arrangement of the oxygen and acetylene removal step downstream of the aqueous condensate separation and the process gas compressor, as carried out in accordance with the invention, represents a particular advantage over WO 2018/153831 A1 cited at the beginning, for example. In a corresponding arrangement, high partial pressures of the components to be converted and a compact design of a reaction unit used for oxygen and acetylene removal can be achieved.

At the same time, at the position proposed according to the invention, sufficient oxygen concentrations for the formation of an ignitable mixture are not yet achieved and the initial conditions after the compressor are in a process window favourable for the removal of oxygen and acetylene, as also explained below. The invention therefore makes it possible to dispense with elaborate security measures otherwise necessary and is more efficient.

Thus, the arrangement proposed in accordance with the invention fulfils all the boundary conditions explained above and achieves a significant advantage in the system design. The positioning of the oxygen and acetylene removal step as provided for in the invention is particularly advantageous if corresponding conditions cannot be created elsewhere in a corresponding separation sequence or positioning there is disadvantageous.

As already mentioned, furthermore specific catalysts and, in particular, favourable catalysis conditions for the removal of acetylene(s) and oxygen from a corresponding gas mixture connected therewith are proposed according to the invention. As also mentioned above, processes known from other areas of technology for the removal of acetylene from gas mixtures are not or not readily applicable for ODH or ODH-E.

For example, an isothermal raw gas hydrogenation can be carried out to remove acetylene from a process gas of a steam cracking process. In this context, reference is made to technical literature such as the article "Ethylene" in Ullmann's Encyclopedia of Industrial Chemistry, online edition, 2009, DOI 10.2002/14356007.a10_045.pub3, and to isothermal raw gas hydrogenation in particular to Falqi, F.: "The Miracle of Petrochemicals. Olefins Industry: An In-Depth Look at Steam-Crackers", Universal-Publishers 2009, ISBN 1-59942-915-2, section "The Linde Raw Gas Hydrogenation System", pages 20 to 22.

The isothermal raw gas hydrogenation takes place in particular after the drying of the raw gas and before the separation of hydrocarbons with two or three carbon atoms. However, hydrogenation of fractions formed in a corresponding separation is also possible in principle, for example isothermal hydrogenation of a fraction of hydrocarbon atoms with two and possibly more carbon atoms after deethanisation and before demethanisation, or adiabatic hydrogenation of a fraction of hydrocarbon atoms with two carbon atoms before formation of an ethane and an ethylene fraction.

In steam-cracking processes or in downstream steps of these, the hydrogenations mentioned above always take place in the absence of molecular oxygen and with carbon monoxide contents of less than 1%, typically less than 1000 ppm by volume. For selective acetylene removal in ethylene-rich streams, precious metal catalysts, for example on palladium basis, are typically used. These may be doped with other precious metals if necessary. The use of nickel catalysts, which however react very sensitively to the carbon monoxide content in the matrix and are therefore only used for carbon monoxide contents of approx. 50 to a maximum of 5,000 ppm by volume, is also known.

Overall, it can be concluded that the catalysts for selective hydrogenation conventionally used in steam cracking processes, such as the precious metal or nickel catalysts mentioned above, cannot be used for the selective hydrogenation process because of the comparatively high oxygen content in a gas mixture from the ODH or ODH-E or the OCM. The reason for this is, in particular, that the additional hydrogenation of oxygen in conventional processes would cause the temperature in the catalyst bed to rise so sharply due to the adiabatic reaction that the hydrogenation of ethylene would be greatly accelerated and thus a high proportion of the product would be lost. In the worst case, total hydrogen conversion and uncontrolled runaway of the reactor will occur.

Furthermore, it is to be expected that conventional catalysts will either be poisoned by the water formed during the reaction of oxygen and thus only have a short service life, or the formation of undesired by-products (polymer, so-called green oil) will be greatly favoured.

Conventional precious metal catalysts also typically have a low tolerance to carbon monoxide, which is also present in a gas mixture from ODH or ODH-E or OCM. Especially at higher carbon monoxide concentrations of several thousand ppm volume fraction, the activity decreases very strongly. Compensation through temperature increase and without significant loss of selectivity is only possible to a limited extent.

For the removal of oxygen and acetylene for the processing of gas mixtures from Fluid Catalytic Cracking (FCC) processes, typically sulfided copper or nickel catalysts are used, which means that there is a possibility of sulfur input into the reaction gas or even continuous sulfurization is required. In general, the use of copper-based catalysts for the removal of oxygen and/or acetylene from gas mixtures from petrochemical processes is also known, for example, from U.S. Pat. Nos. 5,446,232 A, 4,034,062 A, 2,953,608 A, 3,912,789 A, 4,049,743 A, 4,035,433 A and 2,381,707 A. However, the measures proposed within the scope of the present invention are not known or suggested by this prior art.

A combined removal of acetylene and oxygen directly at the outlet of an ODH-E reactor is, as previously mentioned, known for example from WO 2010/115108 A1. Again, however, the proposed measures are not described.

Sulfided nickel or copper catalysts for the purification of gas mixtures from FCC typically require the above-mentioned continuous addition of sulfur (for example in the form of dimethyl disulfide, DMDS) to maintain constant activity and selectivity. However, for ODH or ODH-E, this would mean adding a new impurity, which in turn could contaminate the product. The use of nickel catalysts with comparatively high carbon monoxide content is also critical due to the possible formation of volatile nickel carbonyls.

The catalysts used according to the present invention do not have all the disadvantages of conventional catalysts explained above, in particular when used under the specified catalytic conditions. The catalysts used according to the invention and, if necessary, catalysis conditions unfold their advantageous effects in combination with the positioning of the oxygen and acetylene removal step carried out according to the invention. This is why they are used at this position in the separation sequence according to the invention.

Overall, in view of the circumstances explained, the present invention proposes a process for the production of one or more olefins by forming a reaction feed containing oxygen and one or more paraffins. In the case of ODH-E, the reaction feed essentially contains ethane as paraffin, other paraffins are not present or are present only in small amounts. The methane used in OCM is also a paraffin in this sense. If ODH of higher paraffins is carried out, these paraffins have, in particular, three or four carbon atoms.

In the context of the present invention, furthermore, a part of the oxygen in the reaction feed is reacted with a part of the paraffin(s) to form the olefin(s) by an oxidative process, in particular by oxidative dehydrogenation or oxidative coupling, obtaining a process gas. Again, in ODH-E and OCM a conversion to ethylene takes place, which means that only small amounts of other olefins are formed. In the ODH of higher paraffins, the olefins with the same chain length are preferably formed. The process gas contains at least the unreacted part of the paraffin(s) and oxygen, the olefin(s), one or more acetylenes, carbon monoxide, carbon dioxide and water. This list is not exhaustive. In particular, a corresponding process gas may additionally contain the by-products explained above, especially carboxylic acids with the same chain length as the paraffins used.

The process according to the invention comprises subjecting the process gas or a gas mixture which is formed using at least a part of the process gas, in the order stated herein, partially or completely to condensate separation, compression, at least partial removal of the oxygen and the acetylene(s) and one or more stages of a carbon dioxide removal, wherein the at least partial removal of the oxygen and the acetylene(s) is performed at the same time and by a catalytic reaction using a catalyst containing copper oxide or ruthenium. The catalytic reaction is thus carried out, according to the invention, downstream of a separation of aqueous condensates and a raw gas compressor, but upstream of carbon dioxide removal units, and, as explained below, drying units and, in particular, cryogenic separation units. The catalytic reaction is, furthermore, at least in part performed as a hydrogenation.

If, in the context of the present invention, a catalyst containing copper oxide is used, this advantageously also contains manganese oxide. By using these catalysts, the advantages of appropriate positioning, which have already been explained in detail above, can be achieved. The at least partial removal of the oxygen and the acetylene(s) by the catalytic reaction takes place in particular in one process step, i.e. in only one reaction unit and/or using only one catalyst or catalyst bed. The content of oxygen and of the acetylene(s) is therefore reduced at the same time.

The at least partial removal of the oxygen and the acetylene or acetylenes by catalytic reaction is be carried out in the present invention by hydrogenation of the oxygen and the acetylene or acetylenes, wherein hydrogen can optionally be fed into a corresponding reaction unit. However, embodiments not forming part of the invention could provide for at least partial oxidative removal of at least part of the oxygen wherein the carbon monoxide contained in a corresponding gas mixture is oxidized with the oxygen to form carbon dioxide. Depending on the heat of reaction released, an isothermal reaction unit or an at least single-stage adiabatic reaction unit can be used for oxygen and acetylene removal. The amount of hydrogen optionally fed in and/or the temperature level in the case of hydrogenation, are adjusted in such a way that the reaction of oxygen and acetylene(s) at the same time is as complete as possible. The expected products of this conversion are in particular further ethylene, ethane, carbon monoxide, carbon dioxide and water as well as traces of methane, oxygenates and so-called green oil. These components can be easily removed in existing separation steps.

In a variant of the invention in which the positioning of the oxygen and acetylene removal is carried out in accordance with the invention after condensate separation and compression, a multi-stage carbon dioxide removal can be provided, wherein individual stages of the carbon dioxide removal can also be carried out upstream of the oxygen and acetylene removal. In other words, the at least partial removal of oxygen and acetylene(s) can be carried out downstream of one or more stages of carbon dioxide removal and upstream of one or more further stages of carbon dioxide removal.

Advantageously, downstream of the at least partial removal of the oxygen and the acetylene(s), a drying and one or more separation steps are carried out. In the separation step(s), the components formed during the at least partial removal of the oxygen and the acetylene(s) can be easily separated in the remaining process gas or a corresponding subsequent mixture without the need for additional plant components.

In particular, the downstream separation step(s) are designed in such a way that they not only remove the (by-products) formed during the removal of oxygen and acetylene as intended in the invention, but also other undesirable components such as residual carbon dioxide, residual oxygen and any methane and/or other low-boiling components that may be present.

In the context of the present invention, the removal of oxygen and acetylene in particular creates the basic conditions for the safe performance of these further separation steps (especially in cryogenic distillation). The use of such downstream steps also makes it possible to avoid the complete removal of oxygen upstream. As mentioned before, "removal" here also means a partial removal. The use of the present invention has the particular advantage that further downstream in concentrated low-boiling component streams no ignitable mixtures are formed.

In particular, the complete removal of carbon dioxide does not need to be carried out upstream in the context of the present invention, but can be carried out via corresponding downstream separation steps.

Optionally, the or at least one of the mentioned separation steps can be carried out cryogenically and/or adsorptively within the scope of the present invention. In particular, cryogenic distillation can be used, but it is also possible to use, for example, alternative purification steps such as pressure swing adsorption.

As mentioned above, the process gas or its appropriately treated part or a gas mixture formed using the process gas in the present invention, in which the specified positioning of oxygen and acetylene removal is carried out, is present upstream of the oxygen and/or acetylene removal under particularly favourable conditions. These conditions are explained below with reference to the favourable catalytic conditions for the different catalysts.

In particular, the use of the above-mentioned catalysts and the applied catalysis conditions can achieve a complete or almost complete reaction of oxygen and acetylene, while at the same time there are only minimal losses of ethylene and minimal formation of by-products such as green oil and/or carboxylic acids. In embodiments of the invention a particularly high stability and service life of the catalyst is achieved. In contrast to WO 2018/153831 A1, the catalytic reaction takes place at least partly in the form of hydrogenation and in particular with the addition of hydrogen.

In an embodiment of the present invention, the catalyst containing copper oxide is used, which may also contain manganese oxide in particular. In the context of the present invention, a catalyst which can be used advantageously comprises in particular 7 to 11% copper oxide and 10 to 15% manganese oxide. A corresponding catalyst can be supported in particular on bodies made of suitable carrier materials, for example aluminium oxide. Further properties of the copper oxide-containing catalyst include that the catalyst bodies have different shapes and structures such as tablets, rings, triple rings (triholes) as well as other common shapes and structures, whereby the selected shape is adapted to the requirements corresponding to the process, e.g. minimization of the pressure drop across the catalytic reactor.

The at least partial removal of the oxygen and the acetylene(s) comprises, according to the invention, as repeatedly stated, a catalytic hydrogenation of at least part of the oxygen. The at least partial removal of the oxygen and the acetylene(s) is carried out within the scope of the invention, in particular under reaction conditions which comprise a temperature of 180 to 360° C., in particular 200 to 250° C., further in particular 220 to 240° C., a pressure of 1 to 30 bar abs, in particular of 10 or 15 to 25 bar (abs.), a Gas Hourly Space Velocity (GHSV) of 1,000 to 15,000 $h^{-1}$, in particular of 2,000 to 5,000 $h^{-1}$, further in particular of 3,000 to 4,000 $h^{-1}$, and a ratio of hydrogen to oxygen of 0 to 5. In particular, in the at least partial conversion of oxygen, the ratio of hydrogen to oxygen for the latter's hydrogenation can be in a range of, for example, 1 to 4 or 2 to 3. These are, in particular, molar ratios under the above conditions. The pressures used also depend on the positioning of the oxygen and acetylene removal step as explained several times.

Within the scope of the present invention, it was surprisingly recognized that under the at least partially hydrogenating conditions with respect to oxygen, a conversion of acetylene also occurs. By using these conditions and the catalyst used, a simultaneous reaction of oxygen and acetylene can therefore take place. Without being bound to these explanations in any way, one explanation for this reaction could be that at the temperatures used acetylene decomposes on the catalyst and reacts with oxygen to form carbon monoxide or carbon dioxide. Although an oxygen-hydrogenating catalyst is used, a corresponding reaction occurs with acetylene.

As an alternative to the at least partial hydrogenating reaction, an oxidative reaction of the oxygen via the reaction with the carbon monoxide contained in the product gas could also be carried out in principle, as mentioned in WO 2018/153831 A1. Carbon dioxide is formed as a product therein. Typically, however, the acetylene present decomposes on the catalyst surface and leads to coking with a rapid loss of catalyst activity over time. The invention avoids this disadvantage by the reaction conditions mentioned above.

In the context of the present invention, it could thus be surprisingly shown that under suitable reaction conditions when using the copper oxide-containing catalyst, in particular a catalyst based on copper and manganese oxide, acetylene can also be removed simultaneously without significant loss of activity over time. An addition of hydrogen can further reduce coking due to the presence of acetylene. In other words, in the context of the present invention, instead of oxidizing conditions, such conditions are used which lead to an at least partial hydrogenation of the oxygen.

In an alternative arrangement of the present invention, the catalyst containing ruthenium is used. In the context of the present invention, a catalyst which can be used advantageously in this respect comprises in particular 0.01 to 1% ruthenium. A corresponding catalyst can be supported in particular on bodies made of suitable carrier materials, for example aluminium oxide. Further properties include that the catalyst bodies have different shapes and structures such as tablets, rings, triple rings (triholes) as well as other common shapes and structures, wherein the selected shape is adapted to the requirements corresponding to the process, e.g. minimization of the pressure drop across the catalytic reactor.

When the ruthenium-containing catalyst is used, the at least partial removal of the oxygen and the acetylene or acetylenes comprises a catalytic hydrogenation advantageously carried out under reaction conditions comprising a temperature of 120 to 300° C., in particular of 130 to 170° C., a pressure of 1 to 30 bar abs., in particular of 10 to 25 bar abs., an hourly gas space velocity of 1,500 to 4,500 $h^{-1}$ and a ratio of hydrogen to oxygen of 1 to 14, for example of 4 to 10. The pressures used here also depend on the positioning of the oxygen and acetylene removal step, as explained several times.

In the context of the present invention it has been found that also known ruthenium-containing catalysts are advantageous for the simultaneous hydrogenation of oxygen and acetylene in the present field of application. They show a high tolerance against the strong adiabatic temperature rise mentioned at the beginning. The ethylene loss of less than 2% is also tolerable.

In all cases, in the context of the present invention, the at least partial removal of oxygen and acetylene(s) can be carried out with the addition of hydrogen, either to set reaction conditions suitable for the hydrogenation reactions, or to avoid even the slight decomposition of acetylene during the oxidation of carbon monoxide with oxygen, as mentioned above.

As already mentioned, the present invention can be used in particular in the process for the oxidative dehydrogenation of ethane, wherein the previously explained compositions of the feed mixture and the process gas result or are predetermined.

The present invention also extends to a plant for the production of one or more olefins, in respect of which reference is made to the corresponding independent patent claim. With regard to the features and advantages of this plant, which is advantageously set up to carry out a procedure as explained above in detail in embodiments, reference is made to the explanations above.

The invention is explained in more detail below with reference to the attached drawing as well as to inventive examples and comparative examples in accordance with the invention.

DESIGN EXAMPLES

FIG. 1 illustrates a method according to a particularly preferred embodiment of the present invention and is designated 100 in total. The explanations regarding process 100 apply equally to a corresponding plant in which the process steps shown in FIG. 1 are realised by corresponding plant components.

In process 100, a reaction feed containing oxygen and one or more paraffins is formed and subjected to oxidative dehydrogenation 1 in the form of a material stream a. A process gas formed in the oxidative dehydrogenation is at least partially fed to a condensate separation 2, in which, for example, water and acetic acid are condensatively separated. The corresponding process gas or its part is fed to the condensate separation in the form of a process gas stream b.

The process gas removed from the condensate separation and depleted in water and possibly other components is fed in the form of a process gas flow c to a process gas compressor or raw gas compressor 3 and compressed there to a pressure level of, for example, more than 15 bar. The compressed process gas stream is fed in the form of a material flow d to an at least partial removal 4 of oxygen and acetylenes, in which both acetylenes and oxygen are reacted by setting certain reaction conditions. The correspondingly treated process gas is subjected to carbon dioxide separation 5 in the form of a process gas stream e, then passes through a drying process 6 in the form of a process gas stream f and finally is subjected to one or more further separation steps 7 in the form of a process gas stream g, which are shown here in a highly simplified form. In the separation step(s) 7, one or more fractions h, i are formed and carried out from process 100.

Basically, procedure 100, which is illustrated in FIG. 1, can be implemented in different ways. In particular, process steps 5 to 7 can be carried out in a different arrangement, partial streams or fractions can be recirculated and the like. The embodiment of the present invention was repeatedly explained.

According to Example 1, a commercially available catalyst consisting of copper and manganese oxide supported on alumina was examined for its suitability for use in the removal of oxygen and acetylene from a process gas of the ODH or ODH-E. The catalyst was crushed to 3 mm and filled into a tubular reactor with an inner diameter of 29 mm. Glass beads were filled in as inert material above the catalyst bed. A catalyst bed of 15 cm was realized. The reactor was operated as an adiabatic tube reactor and was heated via heating bands to compensate for heat losses. Gas mixtures with the composition (in volume percent) given in Table 1A were fed in via mass flow controllers:

TABLE 1A

|  | Gas mixture 1 | Gas mixture 2 |
|---|---|---|
| Hydrogen | 0 | 0.66 |
| Ethylene | 35.9 | 35.9 |
| Acetylene | 0.015 | 0.015 |
| Ethane | 59.1 | 52.5 |
| Oxygen | 0.47 | 0.47 |
| Nitrogen | 1.77 | 7.7 |
| Carbon monoxide | 2.72 | 2.72 |

Tables 1B and 10 show the successful simultaneous removal of oxygen and acetylene over a running time of more than 250 hours for the two gas mixtures listed in Table 1A. Between 158.8 hours and 179.2 hours, switching was performed between gas mixture 1 and 2 according to Table 1A, i.e. hydrogen was also added. Both tables 1B and 10 therefore relate to a continuous test.

The reaction conditions used were an hourly gas hourly space velocity (GHSV) of approx. 3,700 h-1, a reactor inlet temperature of 230° C. and a pressure of 20 bar. It is shown that oxygen can be removed both by oxidation of carbon monoxide (in the absence of hydrogen, gas mixture 1) and by hydrogenation (gas mixture 2). The ethylene losses are extremely low in each case.

TABLE 1B (gas mixture 1 according to Table 1A)

| Running time h | 4.7 | 58.6 | 118.5 | 140.1 | 158.8 |
|---|---|---|---|---|---|
| Ethylene loss % | 1.9 | 0.15 | 0.08 | 0.28 | 0.05 |
| Oxygen conversion % | 100 | 100 | 100 | 100 | 100 |
| Acetylene conversion % | 100 | 100 | 100 | 100 | 100 |

TABLE 1C (gas mixture 2 according to Table 1A)

| Running time h | 179.2 | 199.2 | 226.2 | 254.1 |
|---|---|---|---|---|
| Ethylene loss % | 0.00 | 0.00 | 0.00 | 0.00 |
| Oxygen conversion % | 99.8 | 100 | 100 | 100 |
| Acetylene conversion % | 100 | 100 | 100 | 100 |

Figure 2:
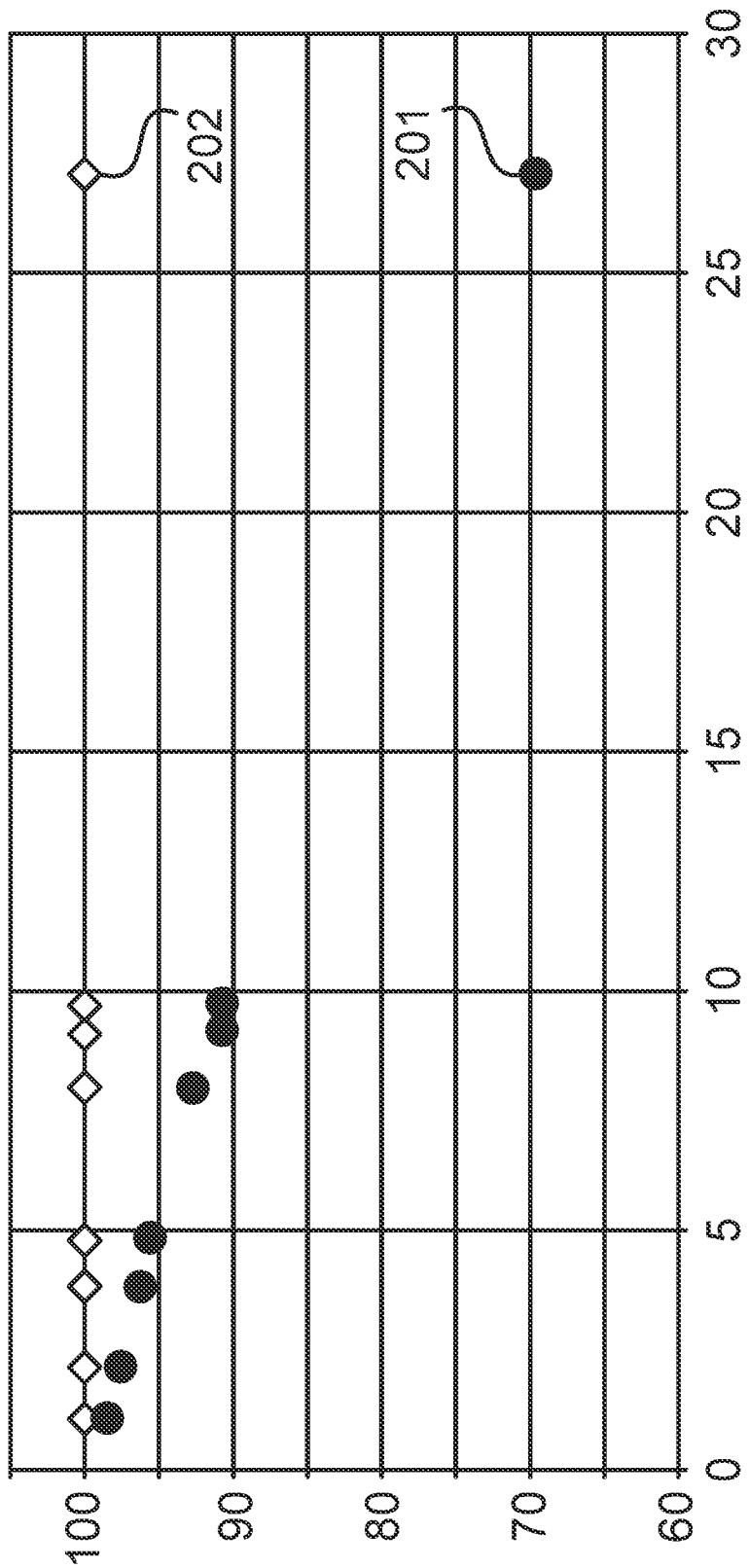
FIG. 2 illustrates data obtained according to an embodiment.

In a Comparative Example 1, the same test set-up as in example 1 was used and the same GHSV was applied. However, only a reactor inlet temperature of 170° C. was used. As shown in FIG. 2, the catalyst is deactivated very quickly under these conditions and the conversion of oxygen decreases. FIG. 2 shows a test time in hours on the abscissa versus a conversion to molar percent on the ordinate. The reaction of oxygen is illustrated with 201 and the reaction of acetylene with 202.

According to example 2, a sample of a commercially available catalyst with ruthenium supported on alumina was examined. The balls (2 to 4 mm diameter) were filled into a tubular reactor with an inner diameter of 29 mm. Glass beads were filled in as inert material above the catalyst bed. A catalyst bed of 20 cm was realized. The reactor was heated by heating bands. The reactor is operated as an adiabatic tube reactor. A gas mixture with the composition (in volume percent) given in Table 2A was fed in via mass flow controllers:

TABLE 2A

| | Gas mixture |
|---|---|
| Hydrogen | 2.06 |
| Ethylene | 34.70 |
| Acetylene | 0.017 |
| Ethane | 39.20 |
| Oxygen | 0.49 |
| Nitrogen | 30.65 |
| Carbon monoxide | 2.89 |

Table 2B shows the successful simultaneous removal of oxygen and acetylene at different conditions. A pressure of 20 bar was set in the reactor.

TABLE 2B

| GHSV h-1 | 2084 | 4340 | 4297 | 2510 |
|---|---|---|---|---|
| Input temperature ° C. | 152 | 150 | 189 | 152 |
| Ethylene loss % | 1.9 | 0.7 | 0.1 | 0.8 |
| Oxygen conversion % | 99.2 | 97.7 | 97.3 | 96.9 |
| Acetylene conversion % | 100 | 100 | 100 | 100 |

In a Comparative Example 2, the same catalyst as in example 2 was tested in the same experimental apparatus with a catalyst bed of 30 cm. The gas mixtures shown in Table 2C (figures in volume percent) were adjusted.

TABLE 2C

| | Gas mixture 1 | Gas mixture 2 | Gas mixture 3 |
|---|---|---|---|
| Hydrogen | 8.36 | 7.82 | 12.41 |
| Ethylene | 37.30 | 35.13 | 35.31 |
| Acetylene | 0.016 | 0.007 | 0.015 |
| Ethane | 48.90 | 53.37 | 45.43 |
| Oxygen | 0.44 | 0.502 | 0.732 |
| Nitrogen | 2.05 | 1.95 | 3.32 |
| Carbon monoxide | 2.92 | 1.22 | 2.77 |

In Comparative Example 2, a pressure of 24 bar was used. The results for the three gas mixtures given in Table 2C are shown in Table 2D. As can be seen from Table 2D, ethylene losses are very high under the specified conditions, especially at the high hydrogen/oxygen ratio.

TABLE 2D

| | Mixture 1 | Mixture 2 | Mixture 3 |
|---|---|---|---|
| GHSV h-1 | 1927 | 2449 | 1961 |
| Input temperature ° C. | 185.5 | 155 | 158.5 |
| Ethylene loss % | 3.2 | 4.2 | 5.5 |
| Oxygen turnover % | 100 | 100 | 100 |
| Acetylene sales % | 98.7 | 99.1 | 99.6 |

The invention claimed is:

1. A process for producing one or more olefins, comprising:
   forming a reaction feed which contains oxygen and one or more paraffins,
   reacting a part of the oxygen in the reaction feed with a part of the paraffin(s) to form the olefin(s) by an oxidative process comprising oxidative dehydrogenation or oxidative coupling of methane, to obtain a process gas, the process gas comprising at least the unreacted part of the paraffin(s) and the oxygen, the olefin(s), one or more acetylenes, carbon dioxide and water, and
   subjecting the process gas or a gas mixture formed using at least a part of the process gas, in the order indicated herein, to
   i) partially or completely to a condensate separation,
   ii) a compression,
   iii) an at least partial removal of the oxygen and the acetylene(s) and
   iv) to one or more stages of carbon dioxide removal (5),
   wherein the at least partial removal of the oxygen and of the acetylene(s) is performed at the same time and by a catalytic conversion using a catalyst comprising copper oxide or ruthenium, and wherein the catalytic conversion is performed at least in part in the form of a hydrogenation.

2. The process according to claim 1 wherein the at least partial removal of oxygen and the acetylene(s) is carried out downstream of one or more stages of a carbon dioxide removal and upstream of one or more further stages of the carbon dioxide removal.

3. The process according to claim 1, in which downstream of the at least partial removal of the oxygen and the acetylene(s), a drying and one or more separation steps are carried out.

4. The process according to claim 1, in which the catalyst containing copper oxide is used and the at least partial removal of the oxygen and the acetylene(s) is carried out under reaction conditions comprising a temperature of 180 to 360° C., a pressure of 1 to 30 bar abs, an hourly gas space velocity of 1,000 to 15,000 $h^{-1}$ and a ratio of hydrogen to oxygen of 0 to 5.

5. The process according to claim 1, in which the ruthenium-containing catalyst is used and the at least partial removal of the oxygen and the acetylene(s) is carried out under reaction conditions which comprise a temperature of 120 to 360° C., a pressure of 1 to 30 bar abs, an hourly gas space velocity of 1,000 to 15,000 $h^{-1}$ and a hydrogen/oxygen ratio of 0 to 5.

6. The process according to claim 1, in which the at least partial removal of the oxygen and the acetylene(s) is carried out with the addition of hydrogen.

7. The process according to claim 1, in which the at least partial removal of the oxygen and the acetylene(s) is carried out isothermally or at least in one step adiabatically.

8. The process according to claim 1, wherein the oxidative dehydrogenation is carried out as oxidative dehydrogenation of ethane.

9. A plant for the production of one or more olefins, which is arranged to form a reaction feed containing oxygen and one or more paraffins, and which is arranged to react a part of the oxygen in the reaction feed with a part of the paraffin(s) to form the olefin(s) by an oxidative process comprising oxidative dehydrogenation or oxidative methane coupling, to obtain a process gas, wherein the process gas contains at least the unreacted part of the paraffin(s) and oxygen, the olefin(s), one or more acetylenes, carbon dioxide and water, characterized in that the plant is configured to subject the process gas partially or completely, in the order indicated herein, to a condensate separation, a compression, an at least partial removal of the oxygen and the acetylene(s) and to one or more stages of a carbon dioxide removal, wherein for the at least partial removal of the oxygen and the acetylene(s) at the same time and by a catalytic conversion a catalyst comprising copper oxide or ruthenium is provided which is adapted to catalyze the catalytic conversion at least in part in the form of a hydrogenation.

10. The plant according to claim 9, which is configured to carry out a process for producing one or more olefins, in which a reaction feed is formed which contains oxygen and one or more paraffins, and in which a part of the oxygen in the reaction feed is reacted with a part of the paraffin(s) to form the olefin(s) by an oxidative process comprising oxidative dehydrogenation or oxidative coupling of methane, to obtain a process gas, the process gas comprising at least the unreacted part of the paraffin(s) and the oxygen, the olefin(s), one or more acetylenes, carbon dioxide and water, characterized in that the process comprises subjecting the process gas or a gas mixture formed using at least a part of the process gas, in the order indicated herein, partially or completely to a condensate separation, a compression, an at least partial removal of the oxygen and the acetylene(s) and to one or more stages of carbon dioxide removal, wherein the at least partial removal of the oxygen and of the acetylene(s) is performed at the same time and by a catalytic conversion using a catalyst comprising copper oxide or ruthenium, and wherein the catalytic conversion is performed at least in part in the form of a hydrogenation.

* * * * *